US00PP20480P2

(12) United States Plant Patent
Hanes

(10) Patent No.: US PP20,480 P2
(45) Date of Patent: Nov. 17, 2009

(54) ***PELARGONIUM* PLANT NAMED 'CLIP SALCON'**

(50) Latin Name: *Pelargonium hortorum*
Varietal Denomination: Clip Salcon

(75) Inventor: Mitchell Hanes, Morgan Hill, CA (US)

(73) Assignee: Goldsmith Seeds, Inc., Gilroy, CA (US)

( * ) Notice: Subject to any disclaimer, the term of this patent is extended or adjusted under 35 U.S.C. 154(b) by 0 days.

(21) Appl. No.: 12/218,881

(22) Filed: Jul. 17, 2008

(51) Int. Cl.
*A01H 5/00* (2006.01)

(52) U.S. Cl. ..... Plt./325

(58) Field of Classification Search ..... Plt./325
See application file for complete search history.

*Primary Examiner*—June Hwu
(74) *Attorney, Agent, or Firm*—S. Matthew Edwards

(57) ABSTRACT

A new *Pelargonium* plant named 'Clip Salcon,' particularly distinguished by the salmon-pink flowers with bars and spots flower patterning, dark foliage, medium vigor, and good branching.

1 Drawing Sheet

Latin name of the genus and species of the plant claimed: *Pelargonium hortorum.*

Varietal denomination: 'Clip Salcon'.

BACKGROUND OF THE NEW PLANT

The present invention comprises a new *Pelargonium*, botanically known as *Pelargonium hortorum*, and hereinafter referred to by the variety name 'Clip Salcon.'

'Clip Salcon' is a product of a planned breeding program. The new cultivar 'Clip Salcon' has salmon-pink flowers with bars and spots flower patterning, dark foliage, medium vigor, and good branching.

'Clip Salcon' originated from a hybridization in a controlled breeding program in Gilroy, Calif. USA. The female parent was an unpatented hybrid seedling identified as '9716-1.' '9716-1' has light salmon color, with lighter foliage, no flower 'confetti' patterning, and is a single flower compared to 'Clip Salcon.'

The male parent of 'Clip Salcon' was an unpatented hybrid seedling identified as '9657-6.' '9657-6' has salmon color, with less stable 'confetti' pattern, petals shatter more readily, and less vigor compared to 'Clip Salcon.'

'Clip Salcon' was selected as one flowering plant within the progeny of the stated cross in 2004 in a controlled environment in Gilroy, Calif. USA.

The first act of asexual reproduction of 'Clip Salcon' was accomplished when vegetative cuttings were propagated from the initial selection in August 2004 in a controlled environment in Gilroy, Calif. USA.

Horticultural examination of plants grown from cuttings of the plant initiated in August 2004 in Gilroy, Calif. USA , and continuing thereafter, has demonstrated that the combination of characteristics as herein disclosed for 'Clip Salcon' are firmly fixed and are retained through successive generations of asexual reproduction.

'Clip Salcon' has not been observed under all possible environmental conditions. The phenotype may vary significantly with variations in environment such as temperature, light intensity and day length.

'Clip Salcon' has not been made publicly available more than one year prior to the filing of this application.

BRIEF DESCRIPTION OF THE NEW VARIETY

The accompanying photographic drawing shows typical flower and foliage characteristics of 'Clip Salcon' with colors being as true as possible with an illustration of this type. The photographic drawing shows a flowering potted plant of the new variety and a close-up of a flower.

DETAILED BOTANICAL DESCRIPTION

The measurements were taken in Salinas, Calif. USA, in June 2008 on plants that were growing in a greenhouse in one gallon pots. Culture of these plants started in April 2008. The plants were approximately 3 months old.

Color Chart used: Royal Horticultural Society Colour Chart (R.H.S.) 2001

BRIEF SUMMARY OF INVENTION

The following observations, measurements, and comparisons describe plants grown in a greenhouse in Gilroy, Calif., USA. The following traits have been repeatedly observed and are determined to be basic characteristics of the new variety. The combination of these characteristics distinguishes this *Pelargonium* as a new and distinct variety.

TABLE 1

DIFFERENCES BETWEEN THE NEW VARIETY AND A SIMILAR VARIETY

| | 'Clip Salcon' | 'Clips Litsaltwo' (U.S. Plant Pat. No. 17,235) |
|---|---|---|
| Foliage | Less zone, larger leaves | More zone, smaller leaves |
| Flowers | Has 'confetti' color pattern | Has no 'confetti' color pattern |
| Plant | Larger plant | Smaller plant |
| Peduncles | Shorter | Longer |

Plant:

*Form, growth and habit.*—Upright and rounded growth habit. Well-branched.

*Plant height.*—10–15 cm.

*Plant height* (*inflorescence included*).—18–23 cm.
*Plant width.*—13–15 cm.

Foliage:
*Arrangement.*—Alternate, simple.
*Immature, leaf color, upper surface.*—RHS 137B. Lower surface: RHS 137C.
*Mature, leaf color, upper surface.*—RHS 137A. Lower surface: RHS 137C.
*Length.*—2.8–3.5 cm.
*Width.*—4.0–4.4 cm.
*Shape.*—Orbicular.
*Base shape.*—Reniform.
*Apex shape.*—Rounded.
*Margin.*—Very slightly and irregularly crenate.
*Texture, upper surface.*—Hirsute at the margins, glandular hairs.
*Texture, lower surface.*—Slightly hirsute; glandular hairs, some with approximately RHS 25A.
*Color of zone.*—Approximately RHS 178B.
*Color of veins, upper surface.*—Indistinct.
*Color of veins, lower surface.*—RHS 146B.
*Petioles color.*—RHS 146B.
*Width of zone.*—0.5–0.8 cm.
*Petioles length.*—2.7–3.0 cm.
*Diameter of petiole.*—0.25 cm.
*Texture.*—Hirsute; glandular hairs; some with RHS 25A.

Stem:
*Color of stem.*—RHS 144A to B.
*Length of stem.*—8–10 cm.
*Diameter.*—0.5–0.7 cm.
*Length of internodes.*—0.5–1.5 cm.
*Texture.*—Hirsute; glandular hairs.

Inflorescence:
*Type.*—An umbel composed of 30–40 flowers and buds.
*Average quantity of inflorescences.*—20.
*Umbel diameter.*—9–10 cm.
*Umbel depth.*—4–5 cm.
*Color of peduncle.*—RHS 187A.
*Length of peduncle.*—10–15 cm.
*Peduncle diameter.*—0.4 cm.
*Texture.*—Hirsute; glandular hairs, some with approximately RHS 25A.
*Pedicel color.*—RHS 176A.
*Length of pedicel.*—2.5–2.7 cm.
*Diameter of pedicel.*—0.15 cm.
*Texture.*—Short hirsute; glandular hairs, some with approxmiately RHS 25A.

Corolla:
*Form.*—Polypetalous, overlapping.
*Number of petals.*—6–8.
*Width of flower.*—4.5–4.7 cm.
*Depth of flower.*—Approximately 1.5 cm.
Color upper and lower petals, upper surface.—RHS N155B but whiter ground color; between RHS 52C and RHS D overlay; RHS 55C at margins; between RHS 42A and RHS42B in irregular sized blotches, spots and bars (occasionally the blotch is ¼ to ½ of the petal); RHS 43C small spots.
Color upper and lower petals, lower surface.—RHS N 155B but whiter; RHS 43C blotches and RHS 55B at the margins.
*Length of upper petals.*—2.0–2.2 cm.
*Width of upper petals.*—1.7–2.1 cm.
*Length of lower petals.*—2.1–2.2 cm.
*Width of lower petals.*—2.0–2.2 cm.
*Petal shape.*—Obovate.
*Apex shape.*—Rounded.
*Margin.*—Entire.
*Petal texture.*—Papillose.
*Number of petaloids.*—1–3.
*Color of petaloids.*—Same as upper.
*Average length of petaloids.*—1.5 cm.
*Average width of petaloids.*—0.7–0.9 cm.
*Duration of flowering.*—Continuous flowering throughout the Summer.
*Lastingness of flowers.*—About one week.

Bud (when sepals first divide):
*Color.*—RHS N 155B with whiter; RHS 44A barring.
*Length.*—1.0–1.3 cm.
*Width.*—0.6–0.8 cm.
*Shape.*—Elliptical.
*Number of sepals.*—5, fused at the base.
*Color of sepals.*—RHS 146C with overlay of anthocyanins of RHS 176A.
*Length of sepals.*—0.9–1.0 cm.
*Width of sepals.*—0.25–0.4 cm.
*Sepal shape.*—Linear to lanceolate.
*Apex shape.*—Acute.
*Margins.*—Entire.
*Texture, upper surface.*—Smooth.
*Lower surface.*—Pilose along margins; hirsute; glandular hairs, some RHS 25A.

Reproductive organs:
*Pistil.*—1.
*Length.*—0.8–0.9 cm.
*Style color.*—RHS 48A.
*Style length.*—0.3 cm.
*Stigma color.*—RHS 47B.
*Number of anthers.*—About 8–9.
*Length filaments.*—0.6–0.7 cm.
*Color of filaments.*—RHS N155B but whiter with RHS 51A at the anther.
*Pollen amount.*—Moderate.
*Color of pollen.*—RHS 28A.
*Fertility/seed set.*—Not observed on this hybrid.

Disease/pest resistance: Disease resistance and/or susceptibility has not been observed on this hybrid.

What is claimed is:

1. A new and distinct variety of *Pelargonium* plant named 'Clip Salcon,' substantially as illustrated and described herein.

* * * * *

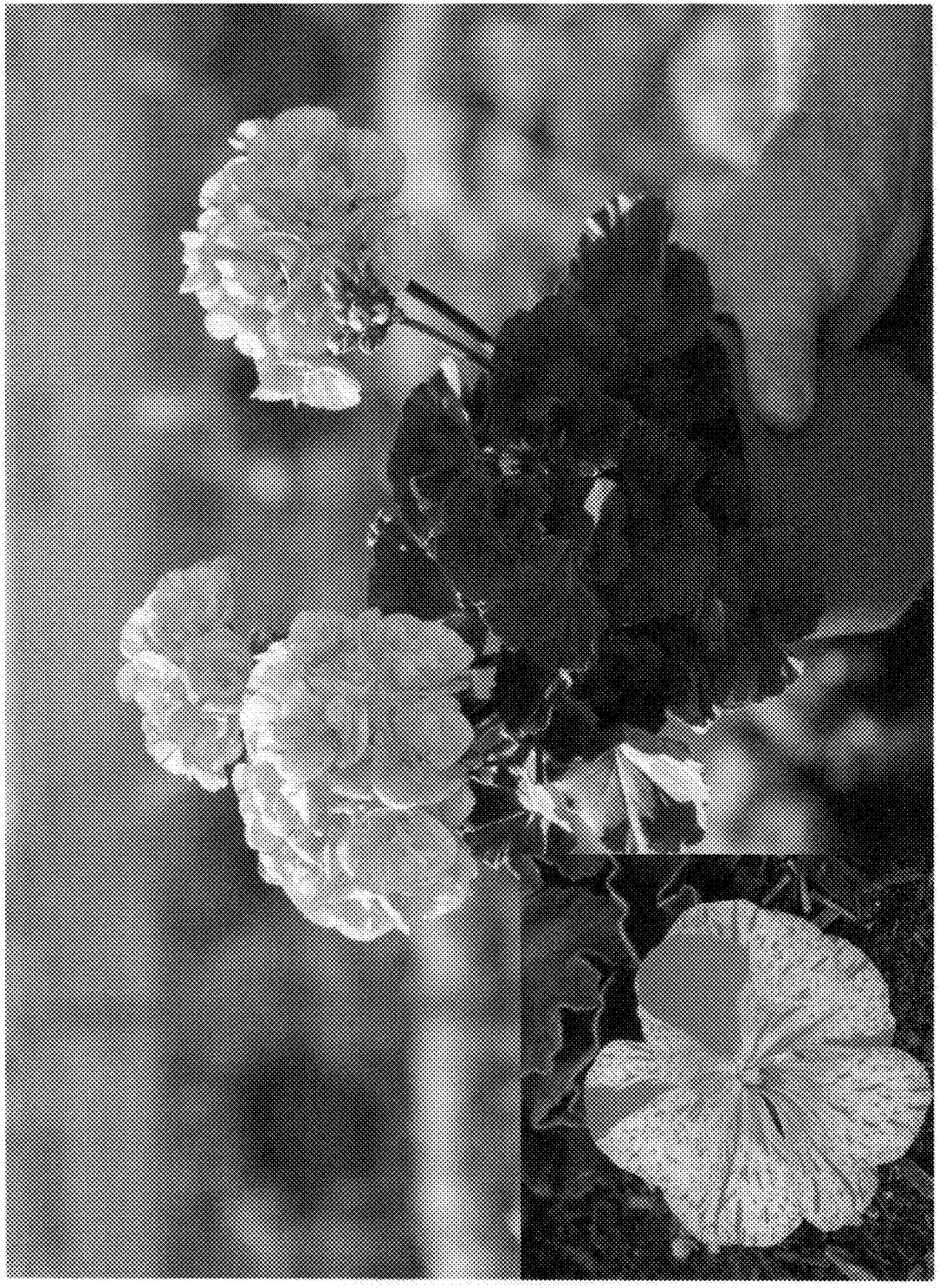

UNITED STATES PATENT AND TRADEMARK OFFICE

CERTIFICATE OF CORRECTION

PATENT NO. : PP 20,480 P2
APPLICATION NO. : 12/218881
DATED : November 17, 2009
INVENTOR(S) : Hanes It is certified that error appears in the above-identified patent and that said Letters Patent is hereby corrected as shown below:

At column 3, line 55, delete "RHS D" and insert therefor --RHS 52D--

Signed and Sealed this

Fifth Day of January, 2010

David J. Kappos

David J. Kappos
*Director of the United States Patent and Trademark Office*